United States Patent [19]

Kobayashi et al.

[11] Patent Number: 4,944,952

[45] Date of Patent: Jul. 31, 1990

[54] METHOD FOR PRODUCING PROCESSED MILK CONTAINING GALACTOOLIGOSACCHARIDE

[75] Inventors: Yoichi Kobayashi; Tatsuhiko Kan; Tsuneo Terashima, all of Tokyo, Japan

[73] Assignee: Kabushiki Kaisha Yakult Honsha, Tokyo, Japan

[21] Appl. No.: 286,719

[22] Filed: Dec. 20, 1988

[30] Foreign Application Priority Data

Dec. 24, 1987 [JP] Japan ................. 62-325488

[51] Int. Cl.⁵ ............................. A23C 9/12
[52] U.S. Cl. ........................ 426/42; 426/61; 426/63
[58] Field of Search ............ 426/42, 43, 67, 63

[56] References Cited

U.S. PATENT DOCUMENTS 2,826,502  3/1958  Sfortunato et al. ............ 426/42
3,852,496  12/1974  Weetall et al. ............ 426/42

FOREIGN PATENT DOCUMENTS 2406393  6/1979  France ............ 426/42
0631133  11/1978  U.S.S.R. ............ 426/42
0700091  12/1979  U.S.S.R. ............ 426/42
0833183  5/1981  U.S.S.R. ............ 426/42

Primary Examiner—Marianne Cintins
Attorney, Agent, or Firm—Oblon, Spivak, McClelland, Maier & Neustadt

[57] ABSTRACT

A method for producing a processed milk containing galactooligosaccharide. An animal milk is treated with a $\beta$-galactosidase derived from *Streptococcus thermophilus* or *Lactobacillus bulgaricus* so as to change, at least 15% of the lactose contained in the animal milk, into galactooligosaccharide expressed by the following general formula:

$$\text{Gal-(Gal)}_n\text{Glc}$$

4 Claims, 1 Drawing Sheet

METHOD FOR PRODUCING PROCESSED MILK CONTAINING GALACTOOLIGOSACCHARIDE

BACKGROUND OF THE INVENTION

The present invention relates to a method for producing a processed milk containing galactooligosaccharide which is a bifidobacterium proliferation accelerating factor.

Galactooligosaccharide represented by a general formula Gal-(Gal)n-Glc (Gal represents galactose residue, Glc represents glucose residue and n represents an integer of 1 to 4)(referred to simply as galactooligosaccharide hereinafter) is one of major components of breast milk oligosaccharide, and is known also as a proliferation accelerating factor of bifidobacterium which is one of useful enterobacteria in human intestines. In recent years, therefore, attempts have been made to mass-produce galactooligosaccharide from lactose or from lactose-containing substances and to add the thus-produced galactooligosaccharide to milk products such as fermented milk and powdered baby milk.

Conventionally, galactooligosaccharide has been produced by, for example, a method in which lactose or a lactose-containing substance is processed by $\beta$-galactosidase produced by Aspergillus oryzae. This method is disclosed in Japanese Patent Publication No. 58-20266 and Japanese Patent Unexamined Publication No. 60-41449. In the known production methods, the galactosyl transfer reaction, which has a priority to mere hydrolysis, takes place only when the lactose content is large. In fact, only hydrolysis takes place materially in processing a material having a lactose content of 10% or less such as ordinary unprocessed milk, skimmed milk and so on.

Therefore, conventional process for producing milk product containing galactooligosaccharide employs a steps of condensing or adding powdered milk to enhance the lactose content in the material milk and effecting an enzyme processing on the material milk to produce galactooligosaccharide from the lactose in the material milk. A method has also been used which employs steps of producing galactooligosaccharide by effecting an enzyme processing on a lactose solution of high lactose content and adding the thus formed galactooligosaccharide to a material milk.

These known methods, however, cannot provide satisfactory result when used in the production of a processed milk containing galactooligosaccharide mainly intended for use as a beverage. Namely, since the material milk such as an unprocessed milk or a skimmed milk cannot be processed directly, the material milk has to undergo condensation, enzyme-treatment and dilution so as to provide milk solid content optimum for drinking. This process is very complicated and, in addition, thermal transformation of milk protein is inevitable in this process.

A method also has been proposed in which galactooligosaccharide prepared from a lactose is added. Such a method, however, requires much cost and is inevitably accompanied by an excessive increase in the total sugar content of the product, resulting in unfavorable effects such as increase in the calorific value and increase in the degree of sweetness. This is because galactooligosaccharide industrially produced from lactose usually contain not only galactooligosaccharide but also di- and monosaccharides in amounts at least the same as that of galactooligosaccharide.

SUMMARY OF THE INVENTION

Accordingly, an object of the present invention is to provide an improved method for producing a processed milk containing galactooligosaccharide, thereby overcoming the above-described problems of the prior art.

To this end, according to the present invention, there is provided a method for producing a processed milk containing galactooligosaccharide comprising: bringing an animal milk into reaction with a $\beta$-galactosidase derived from Streptococcus thermophilus or Lactobacillus bulgaricus so as to change, at least 15% of the lactose contained in the animal milk, into galactooligosaccharide expressed by the following general formula:

$$\text{Gal-(Gal)}_n\text{Glc}$$

where, Gal represents galactose residue, Glc represents glucose residue and n represents an integer of 1 to 4.

The above and other objects, features and advantages of the present invention will become clear from the following description when the same is read in conjunction with the accompanying drawings.

BRIEF DESCRIPTION OF THE DRAWING

The attached sole FIGURE is a graph showing the relationship between rate of generation of glucose and maximum yield of galactooligosaccharide as observed in the beginning 1 hour in a $\beta$-galactosidase treatment.

DETAILED DESCRIPTION OF THE INVENTION

Figure 1:
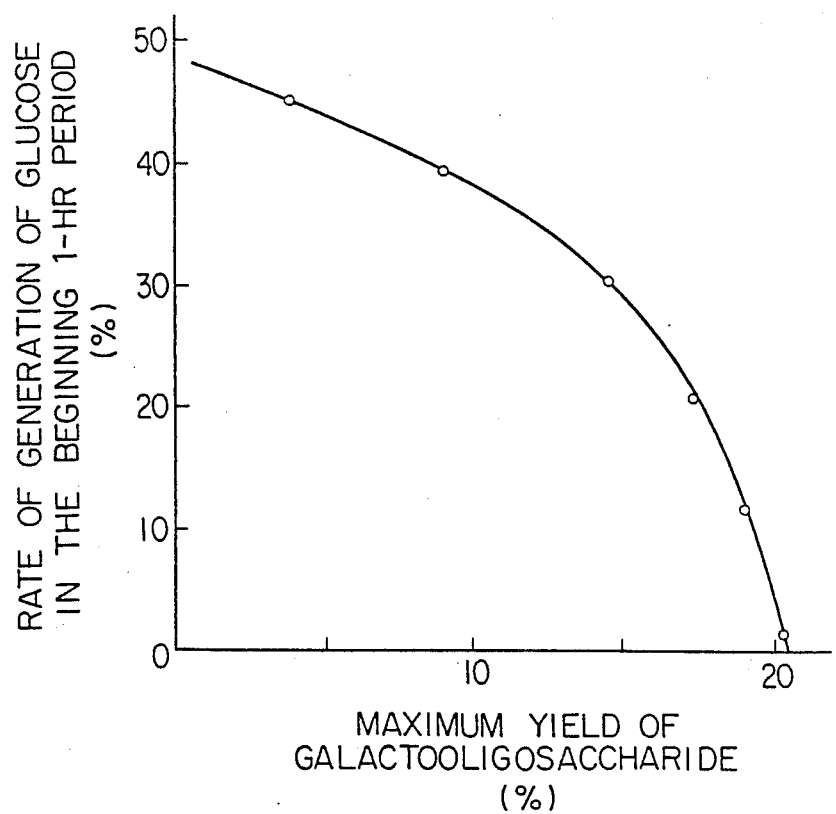

The "$\beta$-galactosidase which is derived from Streptococcus thermophilus or Lactobacillus bulgaricus" used in the method of the present invention has been discovered by the present inventors in the course of an intense study conducted for the purpose of seeking for any enzyme capable of causing $\beta$-galactosyl transition reaction even from a lactose solution of low concentration. The $\beta$-galactosidase specifically causes, at a high yield, $\beta$-galactosyl transition reaction even from a lactose solution of a low concentration such as that of unprocessed milk. In particular, the $\beta$-galactosidase which is derived from Streptococcus thermophilus provides advantageous effects and suitably used as enzyme in the method of the present invention.

Table 1 shows the result of an experiment. The data in Table 1 shows that, in general, it is impossible to produce processed milk containing galactooligosaccharide by a $\beta$-galactosidase treatment directly effected on unprocessed milk. In Table 1, the "yield of galactooligosaccharide" represents the maximum yield which is obtained when a 5% lactose solution was treated with an enzyme of 4 units/lactose g at 40° C. The term "unit" of $\beta$-galactosidase as used in the specification means the level of enzyme activity which can produce glucose at an average rate of 1 $\mu$mol/min at a temperature of 40° C. and in a reaction time of 1 hour from a 2%(w/w) lactose solution which has been adjusted to pH 7.0 by 0.01M phosphoric acid buffer liquid.

TABLE 1

| $\beta$-galactosidase generating bacteria | Yield of galacto-oligosaccharide (%) |
|---|---|
| Aspergillus oryzae | 13.7 |

TABLE 1-continued

| β-galactosidase generating bacteria | Yield of galacto-oligosaccharide (%) |
|---|---|
| Lactobacillus bulgaricus | 15.1 |
| Lactobacillus helveticus | 6.7 |
| Lactobacillus salivarius | 4.7 |
| Lactobacillus fermentum | 3.7 |
| Lactobacillus casei | 0 |
| Lactobacillus acidophilus | 0 |
| Streptococcus latics | 0 |
| Streptococcus thermophilus | 20.2 |
| Bifidobacterium bifidum | 4.9 |
| Bifidobacterium longum | 5.3 |
| Bifidobacterium adolescentis | 9.5 |
| Bifidobacterium breve | 4.3 |
| Bacillus subtilis | 5.5 |
| Kluyveromyces lactis | 5.0 |
| Kluyveromyces fragilis | 4.7 |

A description will be given hereinafter of a method for making a processed milk containing galactooligosaccharide by making use of β-galactosidase derived from Streptococcccus thermophilus or Lactobacillus bulgaricus. The term "β-galactosidase" will be used hereinafter to mean β-galactosidase derived from Streptococcus thermophilus or Lactobacillus bulgaricus unless otherwise specified.

The β-galactosidase used in the reaction can be derived from the extraction of Streptococcus thermophilus or Lactobacillus bulgaricus by various methods such as a method for physically breaking the cellular wall of Streptococcus thermophilus or Lactobacillus bulgaricus by means of supersonic wave or a pressure, a self-digesting method and a method which employs a cellular wall dissolving enzyme, e.g., lisozyme.

The extracted enzyme may be used directly as it is or after refining by a suitable method such as salt precipitation, ultrafiltration and solvent sedimentation. Alternatively, the enzyme may be used in the form of a fixed enzyme. The method also may be such that the bacterium is processed with an organic solvent such as methanol, ethanol, propanol, acetone and toluene or with a surfactant such as sodium dodecyl sulfonate so as to form β-galactosidase-fixed bacterium which is used as the bacterium in the method of the present invention.

Material milks such as cow milk, sheep milk, skimmed cow milk or skimmed sheep milk, and a milk reduced from a powdered milk can be used without any processing. However, the material milk may undergo a concentration control such that the milk solid content and, hence, the lactose content, are increased because the β-galactosidase used in the present invention also has a greater tendency to effect β-galactosyl transfer reaction when the lactose content is large, as in the case of enzymes which have been used conventionally.

Major reactions caused in the enzyme treatment are hydrolytic reactions into glucose and galactose and β-galactosyl transfer reaction into galactooligosaccharide and transfer disaccharide. It is to be understood, however, hydrolysis of generated oligosaccharide takes place even though the transfer reaction is caused, so that the oligosaccharides in the reaction solution is progressively decreased when the reaction time grows long, with the result that the ratio of the monosaccharide becomes greater. Needless to say, it is desirable that the reaction is executed under such a condition as to provide a high yield of galactooligosaccharide, more specifically under a condition which provides an yield of at least 15% with respect to lactose. Any yield below this value cannot provide a processed milk which contains a significant amount of galactooligosaccharide.

The optimum condition for attaining high yield of galactooligosaccharide varies depending on the factors such as the quality of enzyme, composition, in particular lactose content, of the material milk, and so forth. It is to be understood, however, that the most critical requisite is to suppress rapid hydrolysis in the period immediately after the commencement of the enzyme reaction. More particularly, the reaction should be executed in such a manner that the amount of glucose generated with respect to lactose is not greater than 30 wt%, preferably not greater than 25 wt% and more preferably not greater than 20 wt% in one hour from the commencement of the reaction. If this requirement is not met, it is difficult to obtain the maximum galactooligosaccharide yield of 15% or greater, regardless of the total reaction time. This fact will be realized when a reference is made to FIG. 1 which shows the result of an experiment conducted under the same conditions as later-mentioned Example 1 except that the rate of generation of glucose in the period immediately after the commencement of reaction was varied by changing the amount of addition of enzyme.

Therefore, the reaction is preferably conducted in such a manner that the rate of generation of glucose in the period of one hour from the commencement of the reaction does not exceed the above-mentioned upper limit and that the enzyme is de-activated to stop the reaction when the maximum galactooligosaccharide yield has been substantially obtained.

When an unprocessed milk having an ordinary lactose content is treated with β-galactosidase held at optimum temperature and pH value (40 to 60° C. and about pH 6 to 8), it is possible to suppress the hydrolysis in the period immediately after the start of reaction below the above-mentioned limit level and to obtain a processed milk containing about 15 to 20 wt% of galactooligosaccharide in about 2 to 24 hours, by selecting the enzyme concentration to range between about 1 and 100 units /ml. An enzyme concentration below 1 unit/ml makes the reaction speed too low, although an appreciably large maximum galactooligosaccharide is obtained.

The production method of the present invention can be used most suitably in the production of processed milks which are to be served as beverages. The method of the invention, however, can conveniently be used in the preparation of galactooligosaccharide-containing material milk which is used in the production of various products such as milk products including baby milks, lactic acid bacteria beverages, fermented milks, ice creams and condensed milk; milk-containing food such as breads and sweets; and other types of products such as pet-food and calf starter.

Examples of the method of the present invention will be illustrated in comparison with Reference Examples.

EXAMPLE 1

10 of sterilized cow milk having a skimmed milk solid content of 8.2% and a lactose content of 4.5% was heated to 40° C. and was made to react with 4500 units of β-galactosidase derived from Streptococcus thermophilus for 6 hours. The rate of generation of glucose in the beginning 1 hour of the reaction was 12.0 wt% with respect to the amount of lactose in the material milk. Then, the reaction solution was heated to de-activate the enzyme, thereby terminating the reaction.

The product obtained through this process contained 0.94% of galactooligosaccharide, 1.54% of di-saccharide including 0.45% of lactose, and 2.02% of monosaccharide. The product tasted slightly sweet.

EXAMPLE 2

10 of sterilized cow milk having a skimmed milk solid content of 8.2% and a lactose content of 4.5% was heated to 40° C. and was made to react with 4500 units of β-galactosidase derived from *Lactobacillus bulgaricus* for 6 hours. The rate of generation of glucose in the beginning 1 hour of the reaction was 11.5 wt% with respect to the amount of lactose in the material milk. Then, the reaction solution was heated to de-activate the enzyme, thereby terminating the reaction.

The product obtained through this process contained 0.68% of galactooligosaccharide, 1.39% of di-saccharide including 0.41% of lactose, and 2.43% of monosaccharide. The product tasted slightly sweet.

REFERENCE EXAMPLE 1

10 of sterilized cow milk having a skimmed milk solid content of 8.2% and a lactose content of 4.5% was heated to 40° C. and was made to react with 4500 units of β-galactosidase Lactozyme (produced by Novo) derived from *Kluyveromyces fragilis* for 6 hours. The rate of generation of glucose in the beginning 1 hour of the reaction was 18.5 wt% with respect to the amount of lactose in the material milk. Then, the reaction solution was heated to deactivate the enzyme, thereby terminating the reaction.

The product obtained through this process contained 0.45% of galactooligosaccharide, 0.90% of di-saccharide including 0.31% of lactose, and 3.15% of monosaccharide. The product tasted very sweet.

REFERENCE EXAMPLE 2

10 of sterilized cow milk having a skimmed milk solid content of 8.2% and a lactose content of 4.5% was heated to 40° C. and was made to react with 4500 units of βgalactosidase lactase (Y-400 produced by Yakult) derived from *Aspergillus oryzae* for 6 hours. The rate of generation of glucose in the beginning 1 hour of the reaction was 13.0 wt% with respect to the amount of lactose in the material milk. Then, the reaction solution was heated to de-activate the enzyme, thereby terminating the reaction.

The product obtained through this process contained 0.60% of galactooligosaccharide, 2.20% of di-saccharide including 1.95% of lactose, and 1.70% of monosaccharide. The product contained a large quantity of unreacted lactose.

EXAMPLE 3

A skimmed milk of 40° C. and having a skimmed solid content of 10% and lactose content of 5.2% was treated with β-galactosidase (30 units/lactose g) derived from Streptococcus thermophilus. The reaction time was varied between 0.5 hour and 7 hours. Table 2 shows the change in the composition of the saccharide composition in the reaction solution due to change in the reaction time.

As will be understood from this Table, the rate of generation of glucose is as small as 22.5% at 1 hour after the commencement of the reaction and oligosaccharides are generated at high rate.

TABLE 2

| Reaction time (Hr) | Saccharide composition (%) | | | |
|---|---|---|---|---|
| | tetra-saccharide | tri-saccharide | di-saccharide | mono-saccharide |
| 0.5 | 0.3 | 11.2 | 68.4 | 20.0(13.0) |
| 1.0 | 0.8 | 12.7 | 55.3(46.3) | 31.2(22.5) |
| 1.5 | 1.5 | 13.4 | 46.7 | 38.5(25.1) |
| 2.0 | 1.4 | 15.4 | 37.4(16.1) | 45.7(32.7) |
| 3.0 | 2.1 | 15.1 | 28.6(7.4) | 54.1(37.7) |
| 4.0 | 1.5 | 14.5 | 25.4 | 58.6(41.5) |
| 5.0 | 2.7 | 12.7 | 22.1(5.4) | 62.5(42.6) |
| 6.0 | 1.1 | 11.5 | 21.2 | 66.2(44.2) |
| 7.0 | 2.2 | 10.0 | 20.2(4.4) | 67.6(44.5) |

Note: Percents in parentheses in dissaccharide represent lactose.
Percents in parentheses in mono-ssaccharide represent lactose.

As has been described, the method of the present invention makes it possible to produce a processed milk containing galactooligosaccharide by a direct β-galactosidase effected on animal milk. This method is free from problems encountered with conventional methods such as thermal transformation of protein due to condensation of the material milk and increase in the sweetness degree and calorific value attributable to increase in the total sugar content. In addition, the lactose content can be reduced to a level of 20% or below of the initial value, so that the product beverage can be taken safely even by persons suffering from so-called lactose intolerance. Thus, the present invention makes it possible to produce, at a reduced cost, a safe processed milk containing galactooligosaccharide of a high quality suitable for drinking purpose.

What is claimed is:

1. A method for producing a milk product containing galactooligosaccharide comprising: admixing an animal milk with a β-galactosidase derived from Streptococcus thermophilus or lactobacillus bulgaricus at a temperature of 40~60° C., a pH of about 6~8, and an enzyme concentration of 1~100 units/ml wherein the amount of glucose generated in the period of 1 hour from the commencement of enzyme treatment is not greater than 30 wt.% of lactose in said animal milk, so as to convert at least 15% of lactose contained in said animal milk into galactooligosaccharide expressed by the following general formula:

$$\text{Gal-(Gal)}_n\text{-Glc}$$

where, Gal represents galactose residue, Glc represents glucose residue and n represents an integer of 1 to 4.

2. A method according to claim 1, wherein the amount of glucose generated in the period of 1 hour from the commencement of enzyme treatment is not greater than 25wt% of lactose in said animal milk.

3. A method according to claim 1, wherein the lactose content of said animal milk ranges between 2 and 10%.

4. A method according to claim 1, wherein the lactose content of said animal milk ranges between 3 and 8%.

* * * * *